United States Patent
Kong

(10) Patent No.: US 12,337,021 B2
(45) Date of Patent: Jun. 24, 2025

(54) COMPOSITION COMPRISING ELDERBERRY EXTRACT AS EFFECTIVE COMPONENT FOR PREVENTING, TREATING, OR ALLEVIATING ANDROPAUSE SYNDROME

(71) Applicant: Kosa Bio Inc., Gyeonggi-do (KR)

(72) Inventor: Hyun Seok Kong, Seoul (KR)

(73) Assignee: Kosa Bio Inc., Gyeonggi-do (KR)

( * ) Notice: Subject to any disclaimer, the term of this patent is extended or adjusted under 35 U.S.C. 154(b) by 0 days.

(21) Appl. No.: 18/591,599

(22) Filed: Feb. 29, 2024

(65) Prior Publication Data
US 2024/0245742 A1 Jul. 25, 2024

Related U.S. Application Data

(63) Continuation of application No. 17/289,893, filed as application No. PCT/KR2019/013465 on Oct. 15, 2019, now abandoned.

(30) Foreign Application Priority Data

Oct. 31, 2018 (KR) ........................ 10-2018-0131431

(51) Int. Cl.
*A61K 36/35* (2006.01)
*A61P 5/24* (2006.01)

(52) U.S. Cl.
CPC ................ *A61K 36/35* (2013.01); *A61P 5/24* (2018.01); *A61K 2236/00* (2013.01)

(58) Field of Classification Search
None
See application file for complete search history.

(56) References Cited

FOREIGN PATENT DOCUMENTS

CN 109498599 A * 9/2019

OTHER PUBLICATIONS

Mahmoudi, et al., "Antidepressant Activi9ties of Sambucus Ebulus and Sambucus Nigra," 2014 European Review for Medical and Pharmacological Sciences 18(22) pp. 3350-3353.
Rezaee, et al., "Safranal: From an Aromatic Natural Product to a Rewarding Pharmacological Agent," Iranian J Med Sci Jan. 2013, vol. 16 No. 1, pp. 12-26.
Mlynarczyk, et al., "Bioactive Properties of *Sambucus nigra* L. as a Functional Ingredient for Food and Pharmaceutical Industry," Journal of Functional Food, 2018, vol. 40 pp. 377-390.
Vlachojannis, et al., "A Systematic Review on the Sambuci Fructus Effect and Efficacy Profiles," Phytotherapy Research 2010 24 pp. 1-8.
Tariz, et al., "Andropause: Is the Emperor Wearing Any Clothes?" Reviews in Endocrine and Metabolic Disorders 2005, vol. 6 No. 2, p. 77.
Puri and Singh, "Adam and AMS Scale for Assessing Andropause Among Aging Indian Men," International Journal of Pharmacy and Pharmaceutical Sciences, vol. 7, Issue 1, 2015 pp. 453-458.

* cited by examiner

*Primary Examiner* — Michael V Meller
(74) *Attorney, Agent, or Firm* — TROUTMAN PEPPER LOCKE LLP; Ryan A. Schneider; Chris Davis

(57) ABSTRACT

The present invention relates to a composition comprising an elderberry extract as an effective component for preventing, treating, or alleviating andropause syndrome, wherein the elderberry extract of the present invention increases testosterone secretion in sperm cells and andropause syndrome animal models, and thus can be usefully employed as a pharmaceutical or food composition for preventing, treating or alleviating andropause syndrome.

1 Claim, 2 Drawing Sheets

COMPOSITION COMPRISING ELDERBERRY EXTRACT AS EFFECTIVE COMPONENT FOR PREVENTING, TREATING, OR ALLEVIATING ANDROPAUSE SYNDROME

CROSS-REFERENCE TO RELATED APPLICATIONS

This application is a continuation of U.S. patent application Ser. No. 17/289,893 filed 29 Apr. 2021, which is a US National Stage Application claiming priority to PCT/KR2019/013465 filed 15 Oct. 2019, which claims priority to Korean Application No. 10-2018-0131431 filed 31 Oct. 2018, each of which is incorporated herein by reference as if set forth herein in their entirety.

TECHNICAL FIELD

The present invention relates to a composition for preventing, treating or alleviating andropause syndrome, which includes an elderberry extract as an active ingredient.

BACKGROUND

The change in the endocrine system such as menopause occurring in females is called male climacteric since it occurs in males, and this term was first used for the syndrome similar to female climacteric by Werner in 1939.

Men have no menopause like women, but the decrease in androgen increases with age and decreases by 0.2 to 2.0% every year. From the age of 40 to 50, male hormone secretion gradually decreases, and decreases to ½ of the level in the 30s in the 70s and ⅓ of that in the 80s, thereby reducing the sensitivity of target cells to testosterone, which is an active androgen, and exhibiting several climacteric symptoms like women.

When testosterone in the body is below the normal range (12 nmol/L or 350 ng/dL or more), it is called male hypogonadism, and when a hormone level is lowered due to dysfunction of the pituitary-hypothalamus-testicular axis that produces male hormones as a man ages, it is called late-onset hypogonadism (LOH). According to the Korean Male Menopause Society, male climacteric is defined as a clinical and biochemical syndrome that accompanies typical symptoms experienced with aging in men and serum testosterone deficiency to reduce the quality of life and cause an adverse effect on the functions of various organs, and it is academically referred to as late onset hypogonadism (LOH), and generally referred to as andropause syndrome.

The andropause syndrome is closely related to the decrease in testosterone, and includes all of total testosterone, free testosterone, and protein-binding testosterone. After a man turns 40, testosterone produced from the testis or adrenal glands decreases, resulting in a decrease in serum total testosterone and free testosterone and albumin-binding testosterone by 0.4%, 10% or 12% per year. Drinking alcohol is known to reduce the secretion of testosterone by destruction of cells in the testis by acetaldehyde, which is an alcohol-degrading substance, and smoking also decreases testosterone secretion to increase the occurrence of the climacteric syndrome.

Symptoms of the andropause syndrome may include physical decreases in muscle mass and strength, body fat mass and hair and bone density and an increase in visceral fat, and mentally decreases in intellectual activity, cognitive function and spatial orientation, a change in mood such as fatigue, depression and irritability, and sleep disorders. A sexual change is characterized by decreased sexual desire and erectile function. However, the andropause syndrome does not only have the problem of impotence, but also various accompanying symptoms such as dyslipidemia, cardiovascular disease, abdominal obesity, decreased muscle strength, decreased bone density, decreased motivation, and decreased memory and concentration, and when these symptoms are neglected, the quality of life may be threatened.

Meanwhile, elderberry is a stoloniferous and deciduous broad-leaved shrub of the family Caprifoliaceae, and mainly lives along rivers and in woodlands, grows in various soils and well-drained sunny areas, and has cold resistance and moisture resistance to be able to survive even at −20° C. Elderberry is called golden strawberry or golden grape in Korea, contains proteins, carbohydrates, tannin, vitamin C, and various minerals such as potassium, magnesium and calcium and large amounts of polyphenols, anthocyanins and flavonols in its fruits. Due to a high antioxidant property, elderberry has been used as a cold remedy in home remedies, and is known to be effective for diarrhea, abdominal pain, rheumatoid and antimutagenicity.

Korean Patent No. 10-1870940: Health food composition for improving andropause syndrome, containing *Lespedeza cuneata* and red ginseng Korean Unexamined Patent Application Publication No. 2018-0111317: Composition for preventing, alleviating and treating andropause syndrome, containing composite extract of *Cornus officinalis*, Pueraria root and *Lespedeza cuneata* as active ingredient

DISCLOSURE

Technical Problem

The inventors studied berry extracts to develop a therapeutic agent effective for andropause syndrome, and thus confirmed that an elderberry extract among the berry extracts increases testosterone secretion in Leydig cells and andropause animal models, and therefore, the present invention was completed.

Accordingly, the present invention is directed to providing a composition for preventing, treating or alleviating andropause syndrome.

Technical Solution

To attain the above-described purpose, the present invention provides
 a composition for preventing or treating andropause syndrome, which includes an elderberry (*Sambucus nigra*) extract as an active ingredient.
In addition, the present invention provides
 a food composition for preventing or alleviating andropause syndrome, which contains an elderberry (*Sambucus nigra*) extract as an active ingredient.

Advantageous Effects

Since an elderberry extract of the present invention has an excellent effect to alleviating andropause syndrome through a mechanism of increasing a secretion amount of testosterone, which is a male hormone, in Leydig cells as well as andropause syndrome animal model, a composition of the present invention including the extract as an active ingredient can also have an effect of preventing, treating or alleviating andropause syndrome and thus can be effectively used as a pharmaceutical or food composition.

DESCRIPTION OF THE INVENTION

Figure 1:
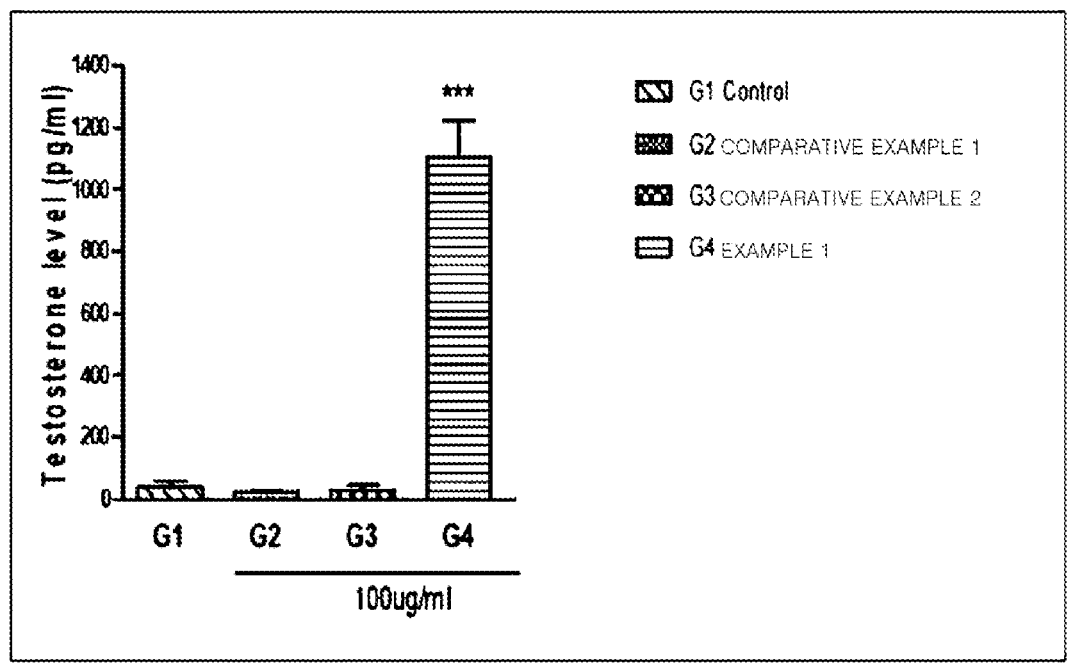
FIG. 1 shows the result of confirming the testosterone secretion capacity of Leydig cells according to the treatment of hydrothermal and ethanol extracts of other types of berries and an elderberry extract.

Hereinafter, the present invention will be described in detail.

The present invention provides a pharmaceutical composition for preventing or treating andropause syndrome, which includes an elderberry (*Sambucus nigra*) extract as an active ingredient.

Elderberry (*Sambucus nigra*) is a preparation called sambucol, which is widely known to have an effect on influenza virus-mediated diseases, but the association with andropause syndrome has not yet been reported.

The andropause syndrome defined in the present invention includes joint or muscle pain, osteoporosis, hyperhidrosis, a sleep disorder, erethism, hypersensitivity, emotional anxiety, lethargy, fatigue, decreased muscle strength, depression, decreased sexual energy, decreased libido, impaired erection, aging, and a decreased genitourinary function.

As a result of a comparative experiment to confirm a testosterone secretion effect in Leydig cells of an elderberry extract according to the present invention with a *Rubus coreanus* water extract and a *Rubus coreanus* ethanol extract, it can be confirmed that the elderberry extract has superior testosterone secretion efficacy.

The composition of the present invention increases a blood testosterone content.

In the present invention, the elderberry extract used as a raw material includes a elderberry solution obtained by infusion or brewing, a concentrate obtained by concentrating a part or all of the same, an extract prepared by drying the concentrate, and a chemical exhibiting the main effect, which is contained in the extract.

The extract of the present invention may be prepared by a conventional method known in the art, for example, maceration, reflux cooling extraction, hydrothermal extraction, room temperature extraction, heat extraction, ultrasonic extraction or supercritical extraction, using a conventional solvent.

Specifically, an extraction solvent selected from distilled water, $C_1$-$C_6$ alcohols, glycerin, $C_2$-$C_6$ alkylene glycols, $C_1$-$C_6$ alkanes, $C_1$-$C_6$ halogenated hydrocarbons, $C_2$-$C_6$ alkyl alkanoates, and a mixture thereof may be used. More specifically, an extraction solvent selected from distilled water, methanol, ethanol, 1,2-propanediol, glycerin, ethylene glycol, butylene glycol, propylene glycol, dichloromethane, dichloroethane, hexane, ethyl acetate and a mixture thereof may be used. Preferably, as a solvent, distilled water may be used.

Here, the amount of the extraction solvent used herein may 5 to 30-fold, and preferably 5 to 20-fold the volume of the weight of a raw material.

An extraction temperature may be selected in the range of various temperatures, for example, 20 to 100° C., which is suitable for an extraction method, by those of ordinary skill in the art, but the present invention is not limited thereto. In addition, an extraction time may vary according to an extraction method by those of ordinary skill in the art, but the present invention is not limited thereto. However, extraction may be performed once or several times for approximately 1 hour to several days. An extract obtained by extraction with a primary extraction solvent may be obtained in a liquid type from which impurities are removed by filtration according to a conventional method, or the liquid extract obtained thereby may be obtained in a powder type by reduced pressure concentration and/or drying according to a conventional method.

In addition, to be used as a composition component, the extract according to the present invention may be a freeze-dried powder type, or a liquid type dispersed or dissolved in water or a conventional organic solvent.

The pharmaceutical composition is preferably prepared by further including one or more types of pharmaceutically acceptable carriers in addition to the above-described active ingredient for administration. The composition of the present invention includes 0.01 to 99 wt % of the elderberry extract with respect to the total weight of the composition. However, the present invention is not limited thereto.

The composition including the extract of the present invention may further include suitable carriers, excipients and diluents, which are conventionally used in the preparation of a pharmaceutical composition.

The composition including the extract according to the present invention may be used after being formulated in an oral form such as a powder, granule, tablet, capsule, suspension, emulsion, syrup or aerosol, a preparation for external use, a suppository, or a sterile injectable solution, and as a carrier, an excipient and a diluent, which can be used herein, lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propyhydroxybenzoate, magnesium stearate and mineral oil may be mentioned. For preparation, a normally used diluent or excipient such as a filler, a thickening agent, a binder, a wetting agent, a disintegrant, or surfactant is used. Solid preparations for oral administration include a tablet, a pill, a powder, a granule, and a capsule, and the solid preparation is prepared by mixing at least one excipient, such as at least starch, calcium carbonate, sucrose, lactose or gelatin with the extract. In addition, other than a simple excipient, lubricants such as magnesium stearate and talc may also be used.

Liquid preparations for oral administration include a suspending agent, an oral liquid for external use, an emulsion and a syrup, and may include various excipients, for example, a wetting agent, a sweetening agent, a fragrance and a preservative, in addition to a frequently used simple diluent, such as water, a liquid or paraffin. Preparations for parenteral administration include a sterilized aqueous solution, a non-aqueous solvent, a suspension, an emulsion, a freeze-dried preparation, and a suppository. As a non-aqueous solvent or suspension, propylene glycol, polyethylene glycol, a vegetable oil such as olive oil, or an injectable ester such as ethyl oleate may be used. As a base for suppositories, Witepsol, Macrogol, Tween 61, cacao butter, laurin, or glycerogelatin may be used.

A preferable dose of the extract of the present invention may vary according to the condition and body weight of a patient, the severity of a disease, a dosage form, or the route and duration of administration, but may be suitable selected by those of ordinary skill in the art. However, for a preferable effect, the extract may be administered at 0.01 mg/kg to 10 g/kg per day, and preferably 1 mg/kg to 1 g/kg per day. The daily dose may be administered once or in divided portions. Therefore, the dose does not limit the scope of the present invention in any way.

The composition of the present invention may be administered to mammals such as a rat, a mouse, livestock, and a human by various routes. All routes of the administration may be expected, and for example, the administration may be performed orally, intrarectally or intravenously.

In addition, the elderberry extract of the present invention may also be used as a food composition for preventing and alleviating andropause syndrome, and may be included at 0.01 to 95 wt %, and preferably, 1 to 80 wt % with respect to the total weight of the food composition.

When the composition of the present invention is used as a food composition, in addition to the elderberry extract as an active ingredient, components that are conventionally added in food production, for example, a protein, a carbohydrate, fats, a nutrient, a seasoning and a flavoring agent may be further added.

Examples of the carbohydrate include conventional sugars, for example, monosaccharides such as glucose and sucrose, disaccharides such as maltose, sucrose and oligosaccharides; and polysaccharides such as dextrin and cyclodextrin, and sugar alcohols such as xylitol, sorbitol and erythritol. A flavoring agent may be a natural flavoring agent and a synthetic flavoring agent.

The food composition of the present invention may be prepared by the same method as the pharmaceutical composition to prevent and alleviate andropause syndrome, and thus may be used as health functional food according to Health Functional Food Act No. 6727 or added to various types of food. In the case when the food composition is prepared for health functional food, the composition can be prepared and processed in a pharmaceutical dosage form such as a powder, a granule, a tablet, a capsule, a pill, a suspension, an emulsion, or a syrup, or in the form of a tea bag, an infused tea or a health drink. When added to various foods, there are no special limitation to the types of food. Examples of food to which the elderberry extract of the present invention may be added may include meat, sausage, bread, chocolate, candy, snacks, confectioneries, pizza, ramen, other noodles, gum, dairy products including ice cream, various soups, beverages, tea, drinks, alcoholic beverages, and vitamin complexes, and include all heath foods in a conventional sense.

In the case when the food composition of the present invention is prepared in the form of a drink, in addition to the elderberry extract of the present invention, citric acid, liquid fructose, sugar, glucose, acetic acid, malic acid or fruit juice may be additionally included.

In addition, the food composition may contain various nutrients, vitamins, electrolytes, flavoring agents, coloring agents, pectic acid and a salt thereof, alginic acid and a salt thereof, an organic acid, a protective colloidal thickening agent, a pH adjuster, a stabilizer, a preservative, glycerin, an alcohol or a carbonating agent used for carbonated beverages in addition to the above-described component. Other than these, the food composition of the present invention may contain natural fruit juice, or a fruit pulp for producing beverages and vegetable beverages. These components may be used independently or in combination.

Hereinafter, preferable examples and experimental examples of the present invention will be described. The following examples and experimental examples were merely described for the purpose of more clearly expressing the present invention, but the disclosure of the present invention is not limited to the following examples.

Example 1: Preparation of Elderberry Extract 100 g of purchased fresh elderberries were added to a 10-fold amount of solvent (1 L) and extracted twice for 2 hours using a reflux cooling device-attached heating mantle, and filtration was performed twice with a 10 to 25-μm filter using a metal detector. Each extract was concentrated to 6.0 to 8.0 brix % using a vacuum concentrator, lyophilized to powder, and stored in a freezer at −20° C. In this experiment, the powdered extract was used after dissolution with distilled water (D.W) per concentration.

Comparative Example 1: Preparation of Rubus coreanus Water Extract

A Rubus coreanus water extract was prepared in the same manner as Example 1, except that fresh berries of Rubus coreanus were used instead of fresh elderberries.

Comparative Example 2: Preparation of Rubus coreanus Ethanol Extract

A Rubus coreanus ethanol extract was prepared in the same manner as Example 1, except that fresh berries of Rubus coreanus were used instead of fresh elderberries, and 70% ethanol was used as an extraction solvent.

Experimental Example 1: Confirmation of Testosterone Secretion Capacity in Cells of Elderberry Extract 1) Culture of Leydig Cells Leydig TM3 cells were obtained from the American Type Culture Collection (ATCC). The Leydig cells were cultured in a $CO_2$ incubator (Forma Scientific, Inc.) using a medium prepared by mixing Dulbecco Modified Eagle Medium (DMEM, high glucose) and Ham's F-12K (Kaighn's) Medium in a ratio of 1:1, and adding 2.5% fetal bovine serum (FBS), 5% horse serum and 1% penicillin-streptomycin. The cells were observed using a microscope to confirm stability, and then the cells were used in the experiment.

2) Evaluation of Testosterone Secretion Capacity in Leydig Cells

TM3 cells were seeded at 1×10⁵ cells/well in a 24-well culture plate, and then stabilized for 24 hours. Afterward, the medium was replaced with a serum-free medium, the extract was diluted according to a concentration (μg/mL) and treated in each well, and then after 24 hours, the medium of each well was recovered. The recovered medium was centrifuged to obtain a supernatant, and to confirm the concentration of testosterone in the supernatant, an assay was carried out based on the method suggested in a testosterone ELISA kit (Abcam®, ab 108666, UK).

Testosterone concentrations produced in the culture of Leydig cells treated with the extract of Example 1, the *Rubus coreanus* extracts of Comparative Examples 1 and 2 were measured using an ELISA kit, and the result is shown in FIG. 1. Referring to FIG. 1, compared with a normal control, a testosterone secretion level was most highly increased in the group treated with the elderberry hydrothermal extract among the groups treated with the *Rubus coreanus* water extract, *Rubus coreanus* ethanol extract and elderberry hydrothermal extract, confirming that the elderberry hydrothermal extract has an effect on the testosterone secretion capacity.

Figure 2:
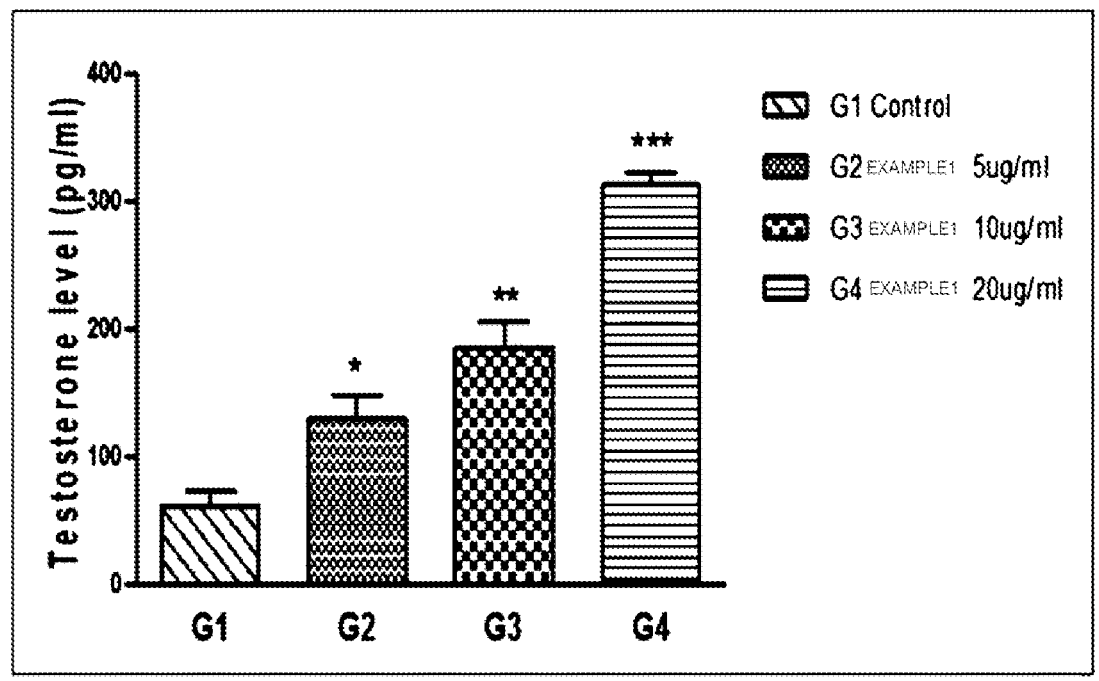
FIG. 2 shows the result of confirming the testosterone secretion capacity according to the concentration-dependent treatment of an elderberry hydrothermal extract in Leydig cells.
Figure 3:
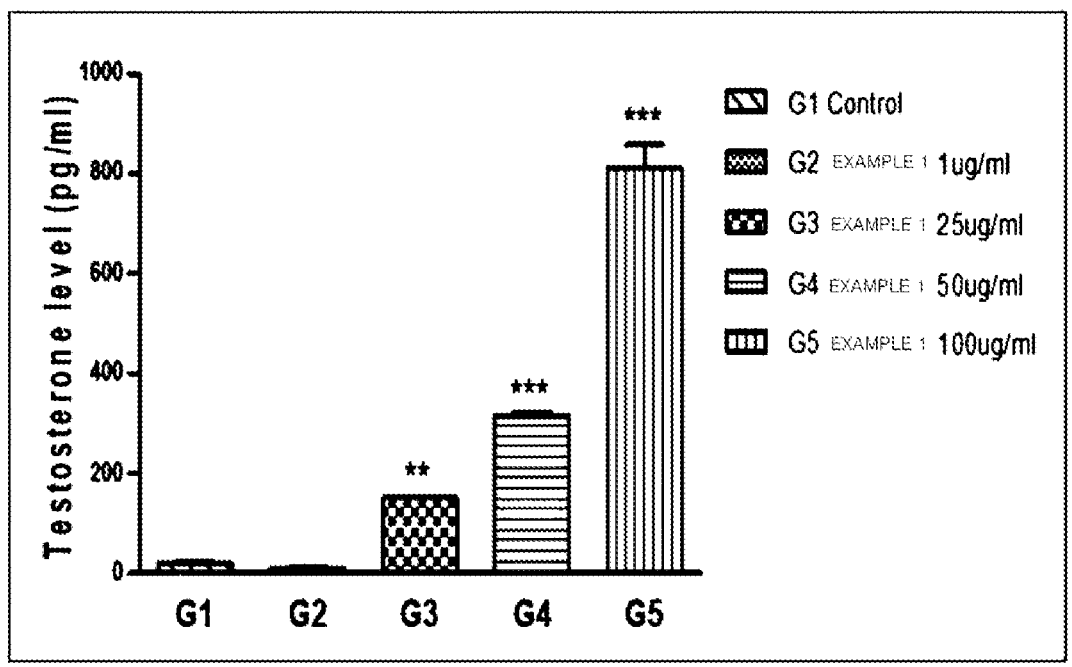
FIG. 3 shows the result of confirming the testosterone secretion capacity according to the concentration-dependent treatment of an elderberry hydrothermal extract in Leydig cells.

To confirm the testosterone secretion effect according to the concentration of an extract, testosterone secretion levels in Leydig cells were measured by treating the elderberry hydrothermal extract at low concentrations (5, 10 and 20 μg/mL) and high concentrations (1, 25, 50 and 100 μg/mL). Referring to FIGS. 2 and 3, compared with the normal control, it was confirmed that the testosterone secretion capacity was concentration-dependently shown from 5 μg/mL or more of the extract, and secretion levels significantly increased. From these results, it was confirmed that the elderberry hydrothermal extract alleviates the andropause syndrome, which is one of the syndromes generated by a hormonal change, particularly, decreased testosterone, by increasing the testosterone secretion capacity in Leydig cells.

Experimental Example 2: Confirmation of Testosterone Secretion Capacity of Elderberry Extract in Andropause Syndrome Animal Model 1) Andropause Syndrome Animal Model and Summary of Test 23-week-old male SD rats (Samtako, Korea) were purchased and acclimated, and upon reaching a body weight of approximately 510 g (6-month-old), they were divided into 9 rats per experimental group. One week before the completion of the experiment, 11-week-old male SD rats (Samtako, Korea) were purchased and acclimated, followed by dividing them into 9 rats per group upon becoming 12 weeks old.

Aa a control group, 6-month-old rats were used, and as an experimental group, elderly rats to which 300 mg/kg of an elderberry hydrothermal extract was orally administered once a day for 12 weeks so as to confirm an improvement in andropause syndrome were used.

2) Evaluation of Testosterone Secretion Capacity in Serum

To analyze the testosterone secretion capacity in serum before autopsy, blood was obtained through jugular vein from rats of all experimental groups. Blood was coagulated for approximately 30 minutes, and then centrifuged for 5 minutes at 10,000 rpm to separate the serum. To confirm a testosterone level in serum after the separation of the serum, analysis was carried out based on a method suggested in a testosterone ELISA kit (Abcam®, ab 108666, UK).

Figure 4:
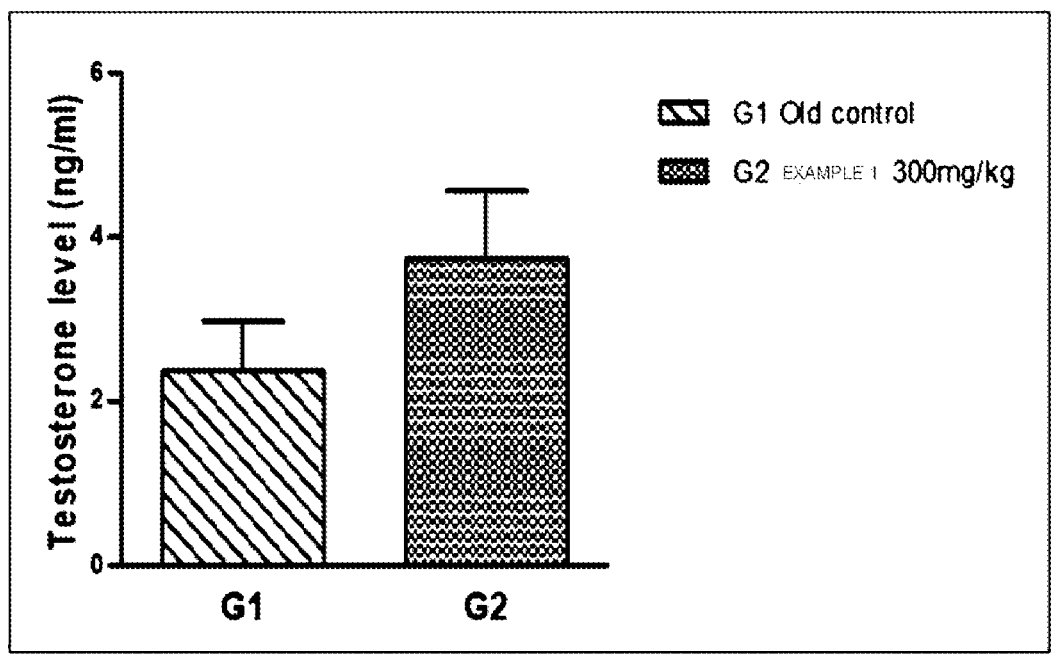
FIG. 4 shows the result of confirming the effect of improving the testosterone secretion capacity according to the treatment of an elderberry hydrothermal extract in elderly animal models.

As a result, compared with the control, a testosterone secretion level was increased, but not significantly, in the group to which the elderberry hydrothermal extract was orally administered, and therefore, it can be confirmed that the elderberry hydrothermal extract has an effect on the testosterone secretion effect (FIG. 4). From these results, it can be confirmed that the elderberry hydrothermal extract increases the testosterone secretion capacity in elderly male rats such that the andropause syndrome, which is one of the syndromes exhibited by a hormonal change, that is, reduced testosterone, is improved.

3) Measurement of Changes in Hepatotoxicity, Lipoprotein and Triglyceride Levels Blood was obtained through an abdominal vein from rats of all groups at autopsy for analysis of biochemical markers in serum. The blood was coagulated for approximately 30 minutes, and then centrifuged for 5 minutes at 10,000 rpm to separate the serum. After separation of the serum, to confirm liver function (AST, ALT), lipoprotein (total cholesterol (T-CHO), HDL cholesterol (HDL-C), LDL cholesterol (LDL-C)) and triglyceride levels, a biochemical analyzer (AU480, BeckmanCoulter, USA) was used, and the result is shown in Table 1.

TABLE 1

| Classification | AST (U/L) | ALT (U/L) | Total cholesterol (mg/dL) | HDL (mg/dL) | LDL (mg/dL) | Triglyceride (mg/dL) |
| --- | --- | --- | --- | --- | --- | --- |
| Young rat control | 99 ± 42 | 30 ± 5 | 65 ± 13 | 40 ± 7 | 20 ± 4 | 45 ± 10 |
| Elderly rat control | 94 ± 39 | 41 ± 22 | 106 ± 19 | 55 ± 8 | 36 ± 10 | 111 ± 44 |
| Elderberry extract-administered group | 98 ± 52 | 30 ± 6 | 93 ± 35 | 49 ± 18 | 32 ± 10 | 74 ± 29 |

As a result, compared with the controls, it can be confirmed that there was no hepatotoxicity in the entire elderberry hydrothermal extract-administered group as there was no statistically significant change, and compared with the control of 12-week-old young rats, in the control of 6-month-old andropause rats, cholesterol and triglyceride levels significantly increased, but these increases were not significant but reduced due to the elderberry hydrothermal extract. From these results, it was confirmed that the elderberry hydrothermal extract has no hepatotoxicity, and is effective in reducing cholesterol and triglycerides.

From the above-described results, it can be seen that the elderberry extract increases the testosterone secretion capacity in Leydig cells as well as andropause syndrome animals to have andropause improvement efficacy.

What is claimed is:

1. A method of treating andropause syndrome characterized by a decrease in the blood testosterone content in a human male in need thereof comprising:
   a) administering a therapeutically effective amount of an elderberry (*Sambucus nigra*) distilled water extract to the human male in need thereof to effectively treat the andropause syndrome in said human male in need thereof, wherein the andropause syndrome has a symptom selected from the group consisting of a sleep disorder, lethargy, fatigue, decreased muscle strength, depression, decreased sexual energy, decreased libido, and impaired erection.

* * * * *